US009958305B2

(12) United States Patent
Nakano et al.

(10) Patent No.: US 9,958,305 B2
(45) Date of Patent: May 1, 2018

(54) GAS SENSOR DEVICE

(71) Applicant: Hitachi Automotive Systems, Ltd., Hitachinaka-shi, Ibaraki (JP)

(72) Inventors: Hiroshi Nakano, Tokyo (JP); Masahiro Matsumoto, Tokyo (JP); Satoshi Asano, Tokyo (JP); Shinobu Tashiro, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 46 days.

(21) Appl. No.: 14/914,231

(22) PCT Filed: Feb. 3, 2014

(86) PCT No.: PCT/JP2014/052386
§ 371 (c)(1),
(2) Date: Feb. 24, 2016

(87) PCT Pub. No.: WO2015/029460
PCT Pub. Date: Mar. 5, 2015

(65) Prior Publication Data
US 2016/0202200 A1 Jul. 14, 2016

(30) Foreign Application Priority Data

Aug. 27, 2013 (JP) ................................. 2013-175449

(51) Int. Cl.
*G01F 1/696* (2006.01)
*G01N 33/00* (2006.01)
(Continued)

(52) U.S. Cl.
CPC ............ *G01F 1/696* (2013.01); *G01F 1/6842* (2013.01); *G01F 1/6845* (2013.01); *G01N 27/18* (2013.01); *G01N 33/0067* (2013.01)

(58) Field of Classification Search
CPC ............ G01N 27/4175; G01N 21/274; G01N 33/0067; G01N 27/18; G01F 1/6842; G01F 1/6845; G01F 1/696
(Continued)

(56) References Cited

U.S. PATENT DOCUMENTS 5,263,369 A * 11/1993 Cutler ..................... G01F 1/684
73/204.15
5,469,749 A * 11/1995 Shimada ................. G01F 1/363
73/721

(Continued)

FOREIGN PATENT DOCUMENTS

JP 5-273168 A 10/1993
JP 6-281607 A 10/1994
(Continued)

OTHER PUBLICATIONS

English Translation of JP 20100151795. Obtained online on May 15, 2017 at <https://worldwide.espacenet.com/>.*

(Continued)

*Primary Examiner* — Harshad R Patel
*Assistant Examiner* — Punam Roy
(74) *Attorney, Agent, or Firm* — Crowell & Moring LLP

(57) ABSTRACT

A gas sensor device of the present invention, aiming sufficient correction results of an internal combustion engine under different operation conditions, includes a concentration sensor for measuring the concentration of gas and a pressure sensor for measuring the pressure of the gas. The gas sensor device also includes a measuring chamber incorporating the concentration sensor and the pressure sensor, and a processing circuit unit that adjusts a signal of the concentration sensor using a signal of the pressure sensor. The processing circuit unit may preferably be provided with a response speed adjusting unit that brings the response (Continued)

speed of a detected signal of the pressure sensor close to the response speed of a detected signal of the concentration sensor.

6 Claims, 15 Drawing Sheets

(51) Int. Cl.
*G01F 1/684* (2006.01)
*G01N 27/18* (2006.01)

(58) Field of Classification Search
USPC .......................................... 73/204.11–204.27
See application file for complete search history.

(56) References Cited

U.S. PATENT DOCUMENTS

| | | | | |
|---|---|---|---|---|
| 7,640,798 | B2* | 1/2010 | Oda | G01F 1/6845 |
| | | | | 73/204.26 |
| 7,752,885 | B2* | 7/2010 | Huang | G01F 1/667 |
| | | | | 73/23.2 |
| 8,359,919 | B2* | 1/2013 | Matsumoto | G01N 27/18 |
| | | | | 73/204.26 |
| 8,468,883 | B2* | 6/2013 | Sakuma | G01F 1/6842 |
| | | | | 73/204.26 |
| 9,372,166 | B2* | 6/2016 | Daamen | G01N 27/18 |
| 9,574,925 | B2* | 2/2017 | Asano | G01F 1/684 |
| 9,618,653 | B2* | 4/2017 | Le Neel | G01W 1/02 |
| 2002/0177017 | A1 | 11/2002 | Nelson et al. | |
| 2008/0148842 | A1* | 6/2008 | Oda | G01F 1/6845 |
| | | | | 73/204.26 |
| 2009/0223820 | A1* | 9/2009 | Ishiguro | G01N 27/419 |
| | | | | 204/424 |
| 2011/0011152 | A1* | 1/2011 | Ito | G01N 27/4074 |
| | | | | 73/23.31 |
| 2011/0107832 | A1* | 5/2011 | Sakuma | G01F 1/6842 |
| | | | | 73/204.26 |
| 2011/0146382 | A1 | 6/2011 | Fleischer et al. | |
| 2013/0036792 | A1 | 2/2013 | Tsuduki et al. | |
| 2014/0102172 | A1* | 4/2014 | Daamen | G01N 27/223 |
| | | | | 73/25.03 |
| 2015/0000394 | A1* | 1/2015 | Knittel | G01D 21/02 |
| | | | | 73/204.18 |
| 2015/0160180 | A1* | 6/2015 | Balsdon | G01F 1/42 |
| | | | | 123/519 |
| 2015/0377676 | A1* | 12/2015 | Asano | G01F 1/684 |
| | | | | 73/861 |

FOREIGN PATENT DOCUMENTS

| | | |
|---|---|---|
| JP | 10-197305 A | 7/1998 |
| JP | 2001-272370 A | 10/2001 |
| JP | 2002-373694 A | 12/2002 |
| JP | 2010-151795 A | 7/2010 |
| JP | 2010-261846 A | 11/2010 |
| JP | 2011-123076 A | 6/2011 |
| JP | 2013-36852 A | 2/2013 |

OTHER PUBLICATIONS

International Search Report (PCT/ISA/210) issued in PCT Application No. PCT/JP2014/052386 dated Mar. 25, 2014, with English translation (four (4) pages).

* cited by examiner

GAS SENSOR DEVICE

TECHNICAL FIELD

The present invention relates to a gas sensor device provided with a sensor element that detects the amount (concentration) of gas.

BACKGROUND ART

Gas sensor devices for measuring the amount of gas are used in various technical fields. Included in the gas sensor devices in the field of the automobiles are humidity sensors which measure the humidity in internal combustion engines to achieve the optimal operation of the internal combustion engines and the concentration sensors which measure the concentration of the fuel in the gas intake passages of the internal combustion engines. These gas sensor devices are also used in the internal combustion engines and the fuel cells that use hydrogen as the fuel of the engines.

The gas sensor devices used in the gas intake passages of the internal combustion engines require, for example, the high degree of accuracy, the stain resistance, the impact resistance and the heat resistance. Meanwhile, the recent internal combustion engines are provided with a variable valve mechanism that changes the timing to open and close the intake and exhaust valves of the combustion chamber to thereby improve the fuel efficiency. The internal combustion engines provided with such a variable valve mechanism induces intensive changes of the flow speed and the pressure of the intake gas in the gas intake passages thereof. In addition, the condition of the intake gas varies depending on the number of cylinders, and the length and the shape of the gas intake passage of the internal combustion engine. Thus, highly accurate measurement of the intake gas in such an environment of the gas intake passage is required.

PTL 1 and 2 disclose a known technique that is arranged to correspond to the change of the flow speed and the pressure of the intake gas in a gas intake passage. PTL 1 (JP 2013-36852 A) as a prior art includes a gas sensor (concentration sensor) that outputs an output value corresponding to the specific component concentration, which is the concentration of a specific gas component contained in gas, and a pressure sensor that measures the pressure of the gas, wherein a provisional specific component concentration is calculated from a concentration sensor value and a pressure sensor value, and the provisional specific component concentration is corrected by using a functional correction value (see Abstract). The pressure sensor and the concentration sensor, or an oxygen sensor, in PTL 1 are separately disposed at an upstream side and a downstream side (in the flow direction of the intake gas), respectively, in the gas intake pipe (gas intake passage) of the internal combustion engine (refer to paragraph 0029). PTL 2 (JP 2010-151795 A) is a prior art that includes an environmental sensor element such as a pressure sensor element, a humidity sensor element, a temperature sensor element and the like, and at least one of these elements is disposed in a measuring chamber, which is positioned farther from a pipe wall than from a bypass route, to thereby reduce the influence of the gas flow and the heat of the pipe wall (refer to paragraph 0015-0027).

CITATION LIST

Patent Literatures

PTL 1: JP 2013-36852 A
PTL 2: JP 2010-151795 A

SUMMARY OF INVENTION

Technical Problem

The concentration sensor and the pressure sensor disclosed in PTL 1 are separately positioned from each other, so the concentration sensor and the pressure sensor are subjected to under different respective pressures in an operational state of a large flow amount zone or a high rotation zone of the internal combustion engine, resulting in an inaccurate correction. This can lead to the inaccurate results of corrections in various operational conditions of the internal combustion engine. If the internal combustion engine operates in a constant rotation speed, the correction value can be led to the optimum correction value by using signals of the rotation speed, the pressure sensor value and the concentration sensor value; however, the reduced or increased rotation speed during acceleration or deceleration of the engine results in the deteriorated accuracy in the correction. Further improved accuracy in the correction requires a larger number of detected signals (the amount of intake gas, the opened degree of a throttle, the rotation speed, the conditions of intake and exhaust valves), thereby excessively increasing the number of man-hours to be altered. In addition, each type of vehicle requires the optimum adjustment in the correction values (the length of a gas intake pipe, the positions of the sensors, the shape of the intake gas).

PTL 2 discloses a configuration wherein a measuring chamber incorporates an environmental sensor element to reduce stains on the environmental sensor, the stains including oil and dust that fly with the flow of the intake gas. The influence of the flow of the gas is concerned in PTL 2; however, unconcerned is the correction of the output of the concentration sensor using the output of the pressure sensor, leaving insufficient consideration about the pressure variation.

PTL 2 does not specifically describe a humidity sensor element that is one type of the environmental sensor element. Meanwhile, PTL 1 describes a system in which a ceramic substrate is provided thereon with a moisture sensitive film to thereby detect electric resistance and electrostatic capacitance (refer to paragraph 0058 of PTL 1). Such an electrostatic capacitor type sensor uses a principle wherein the dielectric constant of a moisture sensitive film changes as the moisture sensitive film absorbs and releases moisture. Because of such principle, the electrostatic capacitor type sensor has a response speed of several seconds to several tens of seconds with respect to the humidity variation, which is a relatively slow response. The pressure sensor, on the other hand, has a high speed response characteristic since it detects a diaphragm deformation. Corrections using different sensor values may involve excessive corrections or unneeded corrections. Using the sensor values of different response speeds can adversely result in an excessive correction and an unnecessary correction.

An object of the present invention is to provide a gas sensor device that can achieve proper correction results under a variety of operation conditions of internal combustion engines.

Solution to Problem

A gas sensor device of the present invention, which solves the problem mentioned above, includes a concentration sensor that measures the concentration of gas and a pressure sensor that measures the pressure of the gas. The device includes a measuring chamber that is isolated from the air flow and that incorporates the concentration sensor and the pressure sensor and a processing circuit unit that adjusts a signal of the concentration sensor by using a signal of the pressure sensor. The processing circuit unit may preferably be provided with a response speed adjusting unit that brings the response speed of a detected signal of the pressure sensor close to the response speed of a detected signal of the concentration sensor. In addition, the concentration sensor in the present invention may preferably have the system of measuring the concentration of gas by using the characteristic of a heat resistance body such that the amount of heat radiation of the heat resistance body varies depending on the concentration of the gas. This system is more effective. Moreover, the concentration sensor in the present invention may include a semiconductor substrate provided with a thin part, wherein the thin part is provided with a heat resistance body.

Advantageous Effects of Invention

According to the present invention, the concentration sensor and the pressure sensor are located under the same pressure in the same space, whereby accurate pressure values are used to provide accurate corrections. This can provide a gas sensor device of highly accuracy such that the device provides proper correction results under a variety of operation conditions of internal combustion engines.

Embodiments of the present invention, which will be described hereinafter, will clarify objects in addition to the objects described above, as well as the configurations and the effects thereof.

DESCRIPTION OF EMBODIMENTS

Embodiments of the present invention will be described below.

First Embodiment

With reference to FIGS. 1 to 8, a gas sensor device according to a first embodiment of the present invention will be described.

Figure 1:
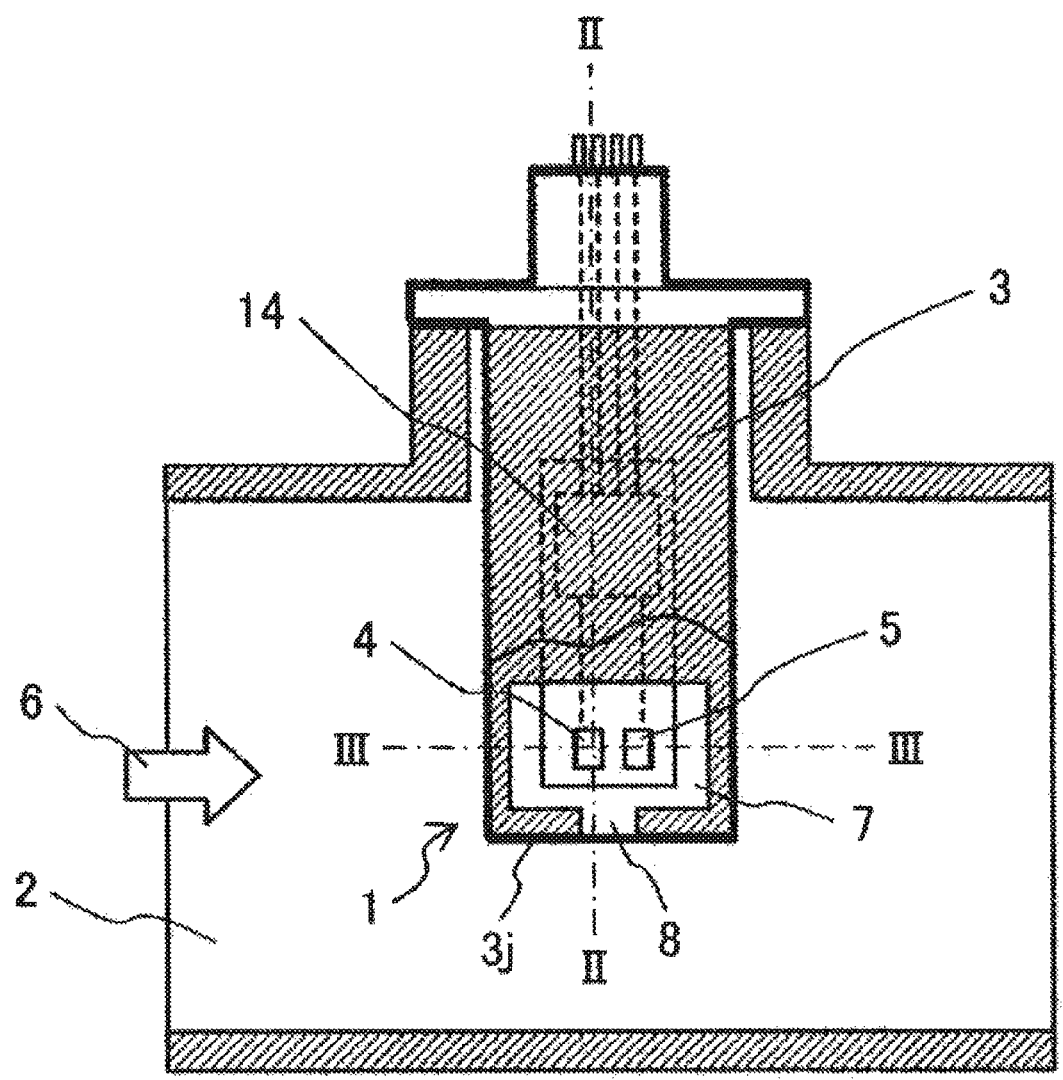
FIG. 1 is a cross sectional view illustrating an embodiment of a gas sensor device of the present invention and a structure in which the gas sensor device is installed.

FIG. 1 illustrates in cross section the gas sensor device of the first embodiment and a structure in which the gas sensor device is installed. The gas sensor device 1 is placed in the gas intake passage 2 of an internal combustion engine so as to protrude inwardly of the passage 2. The gas sensor device 1 has a housing 3 incorporating a humidity sensor element 4 that serves as a detecting element (concentration sensor element) for detecting the amount of gas, and a pressure sensor element 5 for detecting the pressure of the gas intake passage 2. The housing 3 further incorporates a measuring chamber 7 that is isolated from the flow of an intake gas 6 flowing in the gas intake passage 2. The measuring chamber 7 includes a communication path 8 through which the interior of the measuring chamber 7 is communicated with the gas intake passage 2, whereby the intake gas (air) 6 flowing in the gas intake passage 2 is fed into the measuring chamber 7. The humidity sensor element 4 and the pressure sensor element 5 are disposed inside the measuring chamber 7, and are thus located under the same pressure. The humidity sensor element 4 and the pressure sensor element 5 are exposed to the intake gas fed from the same communication path 8. The measuring chamber 7 and the communication path 8 function to restrain the direct flow of the intake gas 6, flowing in the gas intake passage 2, with respect to the humidity sensor element 4. Specifically, the measuring chamber 7 is isolated from the flow of the intake gas (air flow) flowing in the gas intake passage 2. Placement of the humidity sensor element 4 and the pressure sensor element 5 in the measuring chamber 7 prevents exposure of the humidity sensor element 4 and the pressure sensor element 5 with respect to the flow of the intake gas 6 flowing in the gas intake passage 2. This reduces the flowing movement of the air around the humidity sensor element 4, thereby providing a stabilized gas condition where a highly accurate measurement of the humidity can be accomplished.

The humidity sensor element 4 functions to detect the concentration of steam, and is thus included in the category of the concentration sensor. The below explanations indicate the concentration sensor as a humidity sensor.

The communication path 8 is provided to the housing 3 at a bottom portion 3*j* of the housing 3. The bottom portion 3*j* of the housing 3 has a side surface that is disposed substantially in parallel with the flow direction of the intake gas 6 flowing in the gas intake passage 2. The communication path 8, through which the intake gas 2 is fed, extends, from the bottom portion 3*j* toward the measuring chamber 7, in a direction substantially perpendicular to the flow direction of the intake gas 2. The communication path 8 has a cross section in a direction perpendicular to the direction along which the communication path 8 communicates, and the cross section may have a circular shape or a rectangular shape, and may be composed of a slit/slits or a plurality of holes. The communication path 8 has a capacity that is preferably much smaller than that of the measuring chamber 7. The shape of the communication path 8 reduces a direct flow of the intake gas 6 into the measuring chamber 7.

Figure 2:
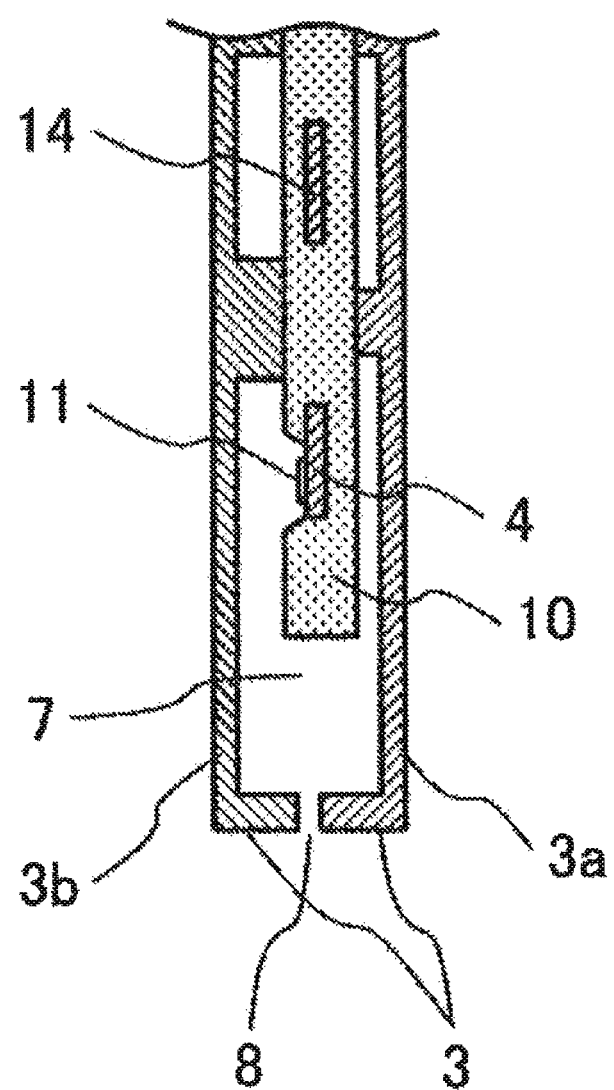
FIG. 2 is a cross sectional view along the line II-II in FIG. 1.
Figure 3:
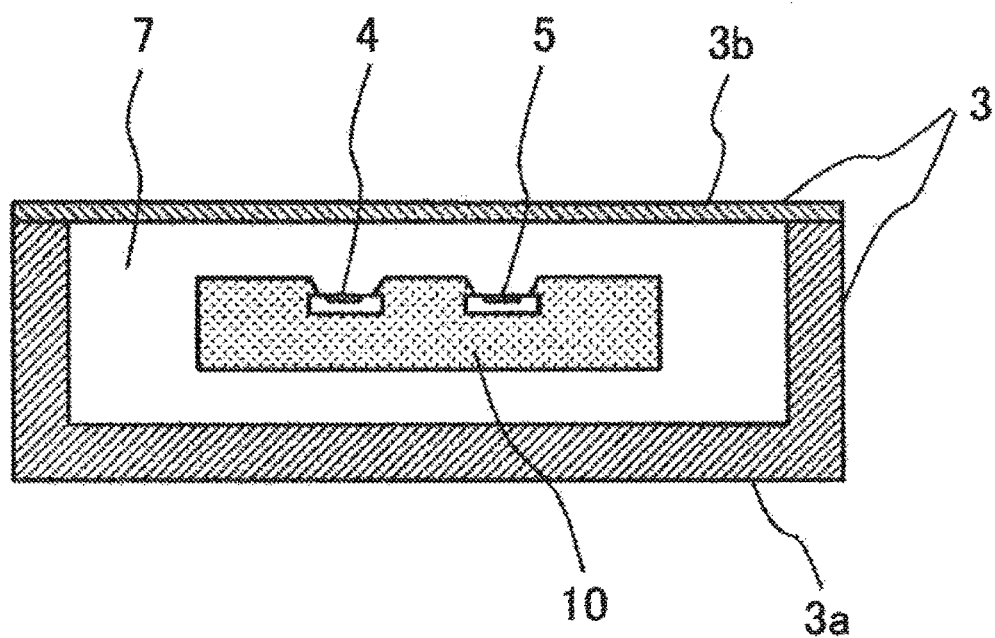
FIG. 3 is a cross sectional view along the line III-III in FIG. 1.

FIG. 2 illustrates a cross sectional view along the line II-II in FIG. 1, and FIG. 3 illustrates a cross sectional view along the line III-III in FIG. 1. As illustrated in FIG. 2, the humidity sensor element 4 is mounted to a sensor package 10 that functions as a support member. The sensor package 10 is packaged by an injection molding technique, enclosing and sealing therein the humidity sensor element 4 with sealing resin. The humidity sensor element 4 has a detecting portion 11 that is packaged in a manner of exposure from the sealing resin. With such a configuration, the humidity sensor element 4 being integral with the sensor package 10 and disposed inside the measuring chamber 7 of the housing 3 is able to measure the humidity of the air inside the measuring chamber 7 using the detecting portion 11 exposed inside the measuring chamber 7.

The pressure sensor element 5 is packaged inside the sensor package 10 by an injection molding technique, in the manner similar to the humidity sensor element illustrated in FIG. 2. The pressure sensor element 5 has a surface that may be covered with a protection film that deforms by pressure. With such an arrangement, the pressure sensor element 5 integral with the sensor package 10 is disposed inside the measuring chamber 7 of the housing 3. The pressure sensor element 5 has a detecting portion that measures the pressure of the air inside the measuring chamber 7.

As illustrated in FIGS. 2 and 3, the housing 3 consists of a base 3*a* and a cover 3*b*. The sensor package 10 enclosing the humidity sensor element 4 and the pressure sensor element 5 is covered with the base 3*a* and the cover 3*b*. The base 3*a* and the cover 3*b* each are die molded and are adhered or joined with each other, thereby forming the measuring chamber 7 and the communication path 8.

Figure 4:
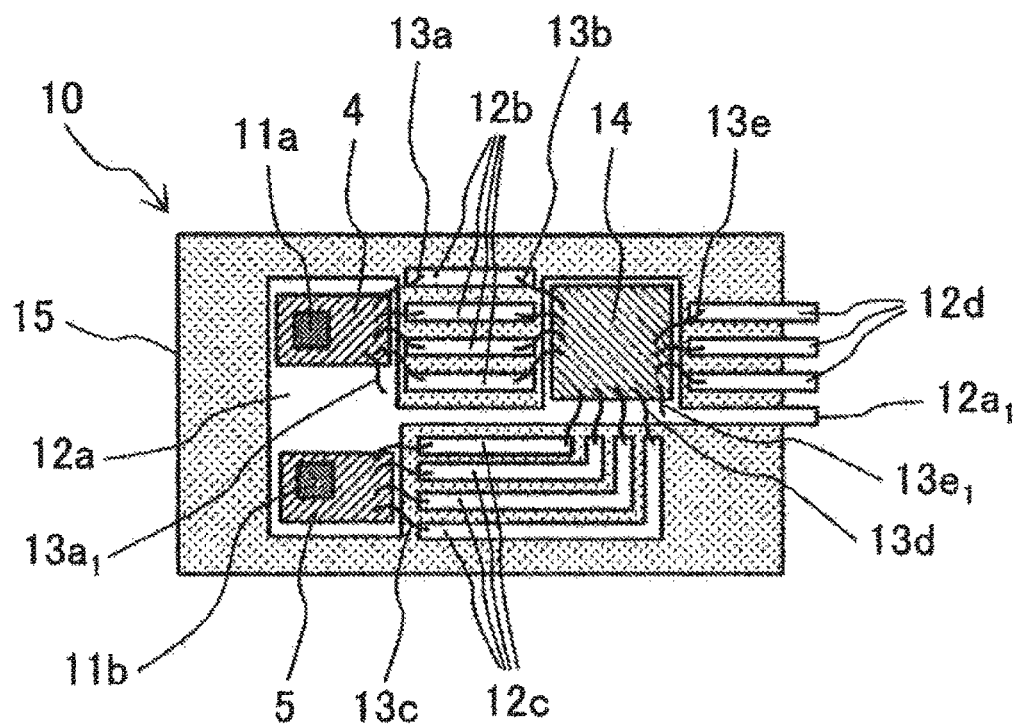
FIG. 4 is a plan view illustrating an internal structure of a sensor package illustrated in FIG. 2.

FIG. 4 illustrates an internal structure of the sensor package 10. Being integral with the sensor package 10 by the sealing of the sealing resin 15 are, in addition to the humidity sensor element 4 and the pressure sensor element 5, lead frames 12*a*, 12*b*, 12*c*, 12*d*, a semiconductor chip 14, and wires 13*a*, 13*b*, 13*c*, 13*d*, 13*e*. The humidity sensor element 4 and the pressure sensor element 5 are adhered on and secured to the lead frame 12*a*. That is, the humidity sensor element 4 and the pressure sensor element 5 are adhered on the same support member (lead frame 12*a*).

The humidity sensor element 4 has an electrode (not illustrated) that is connected, by means of a wire bonding method, to the lead frame 12*b* via the wire 13*a*. The humidity sensor element 4 has a ground electrode that is connected to the lead frame 12*a* via a wire $13a_1$. The lead frame 12*b* is electrically connected to an input electrode (not illustrated) of the semiconductor chip 14 via the wire 13*b*. The pressure sensor element 5 has an electrode (not illustrated) that is connected, by means of a wire bonding method, to the lead frame 12*c* through the wire 13*c*. The lead frame 12*c* is electrically connected to an input electrode (not illustrated) of the semiconductor chip 14 via the wire 13*d*.

The lead frame 12*d* is electrically connected to an output electrode of the semiconductor chip 14 through the wire 13*e*. The semiconductor chip 14 has a ground electrode that is connected to the lead frame 12*a* through a wire $13c_1$.

The semiconductor chip 14 is composed of a semiconductor integrated chip produced by a semiconductor process and configures a processing circuit of the gas sensor device 1. The semiconductor chip (processing circuit unit) 14 includes a driving circuit of the humidity sensor element 4 and a detecting circuit for measurement of the humidity. The semiconductor chip 14 further includes a driving circuit of the pressure sensor element 5 and a detecting circuit for measurement of the pressure. The semiconductor chip 14 is adhered on and secured to the lead frame 12*a* on which the humidity sensor element 4 and the pressure sensor element 5 are adhered. The semiconductor chip 14 has a power source line and a detected signal (output signal line) that are connected to the lead frame 12*d* via the wire 13*e*. The lead frame 12*d* has an end portion that is pulled outside the sensor package 10 as a terminal for an external connection. The lead frame 12*a* connected through the wires $13a_1$, $13e_1$ to the ground electrodes of the humidity sensor element 4 and the semiconductor chip 14 has an end portion $12a_1$ that is pulled outside the sensor package 10 together with an end portion of the lead frame 12*d*.

The lead frame 12*a* in this embodiment functions as a common grounding terminal and is used as a member on which the humidity sensor element 4, the pressure sensor element 5 and the semiconductor chip 14 are mounted. As described above, the humidity sensor element 4, the pressure sensor element 5, the lead frames 12*a*-12*d*, the semiconductor chip 14 and the wires 13*a*-13*e* are packaged by the sealing of the sealing resin 15 so as to expose the detecting portion 11*a* of the humidity sensor element 4, the detecting portion 11*b* of the pressure sensor element 5 and the end portions of the lead frames 12*d*, 12*a*.

Figure 5:
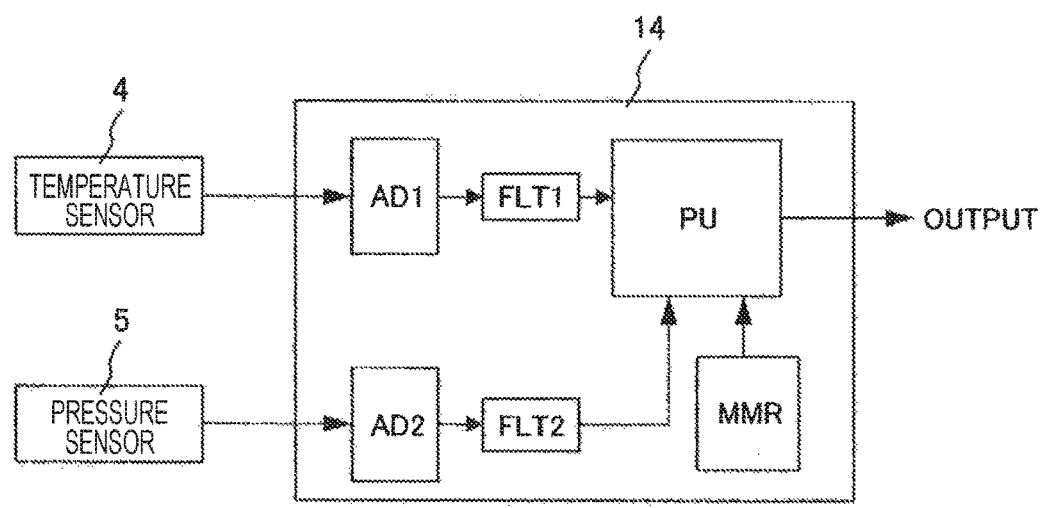
FIG. 5 is a block diagram illustrating a processing mode of a sensor signal in this embodiment.

FIG. 5 illustrates a processing mode of a sensor signal of the semiconductor chip 14. The sensor chip 14 includes an A/D converter AD1 and an A/D converter AD2. The converter AD1 inputs an analog signal sent from the humidity sensor 4 and converts the input signal into a digital value. The converter AD2 inputs an analog signal sent from the pressure sensor element 5 and converts the input signal into a digital value. The humidity signal converted into the digital value in the A/D converter AD1 is subjected to the removal of a signal noise in a signal processing unit FLT1 and is then input in a calculation unit PU. The pressure signal converted into the digital value in the A/D converter AD2 is subjected to the removal of a signal noise in the signal processing unit FLT2 and is then input in the calculation unit PU. The calculation unit PU performs a correction calculation of the humidity signal. The correction calculation determines the amount of correction on the basis of the pressure signal value and a fixed number stored in advance in a memory unit MMR, and the determined correction amount is added to the humidity signal. Then, the humidity signal corrected in the calculation unit PU is output as OUTPUT.

Figure 6A:
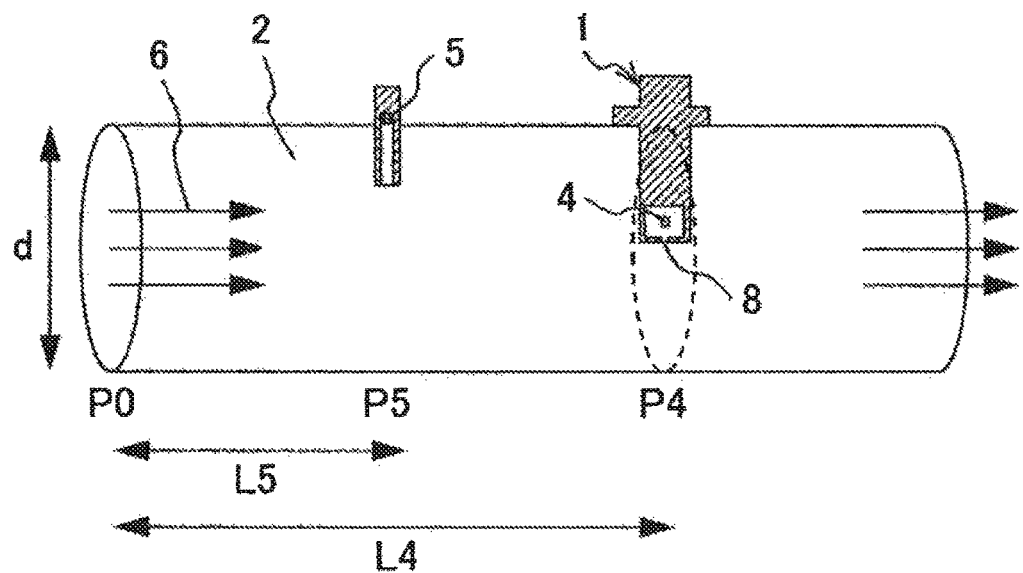
FIG. 6A illustrates a simple model in which a humidity sensor element and a pressure sensor element are disposed in the up-down flow direction, in a separated manner, in a gas intake passage.
Figure 6B:
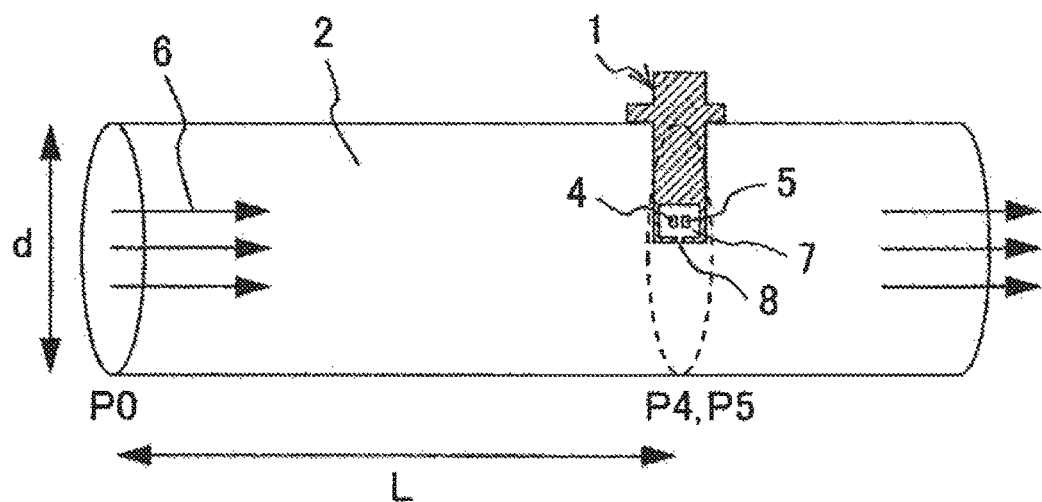
FIG. 6B illustrates a simple model in which a gas sensor device of this embodiment is disposed in the gas intake passage of an internal combustion engine.

The gas sensor device 1 in this embodiment has the following operations and effects that will be described below. FIG. 6A illustrates a simple model in which a humidity sensor element 4 and a pressure sensor element 5 are separately positioned in a gas intake passage 2 in the up-and-down stream direction thereof. FIG. 6B illustrates the gas sensor device 1 of a simple model according to the embodiment, which is positioned in a gas intake passage 2 of an internal combustion engine.

As illustrated in FIG. 6A, the intake gas 6 flows in the gas intake passage 2. The gas intake passage 2 receives the atmospheric pressure indicated by P0 at the left side thereof, receives the pressure (static pressure) indicated by P4 at the position where the humidity sensor element 4 is disposed, and receives the pressure (static pressure) indicated by P5 at the position where the pressure sensor element 5 is disposed. In the system of FIG. 6A, the distance L4 from the left end of the gas intake passage 2 to the humidity sensor element 4 is different from the distance L5 from the left end of the gas intake passage 2 to the pressure sensor element 5. On the other hand, in the system of FIG. 6B in which the present invention is applied, the gas sensor device 1 is positioned at the distance L from the left end of the gas intake passage, and both the humidity sensor element 4 and the pressure sensor element 5 are disposed in the measuring chamber 8. The measuring chamber 8 into which the air is fed through a single number of communication path 8 has inside thereof a uniform pressure. Thus, with regard to the pressure, the span from the left end of the gas intake passage 2 to the humidity sensor element 4 and the span from the left end of the gas intake passage 2 to the pressure sensor element 5 have the same distance L.

Figure 7A:
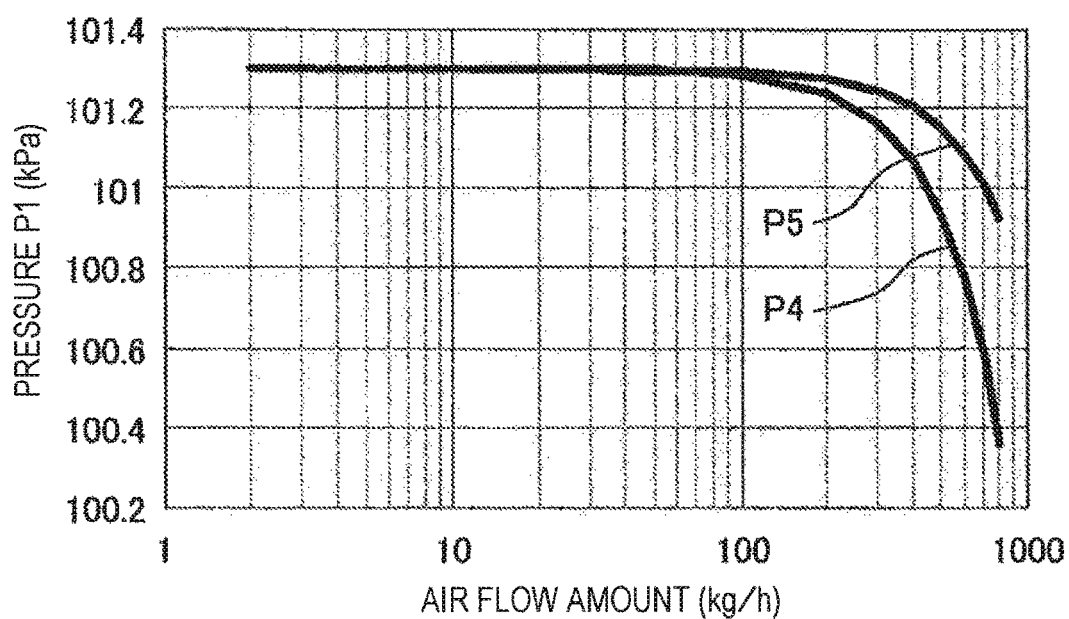
FIG. 7A is a graph indicating the pressure at the position of the humidity sensor element and at the position of the pressure sensor element, in the system illustrated in FIG. 6A.
Figure 7B:
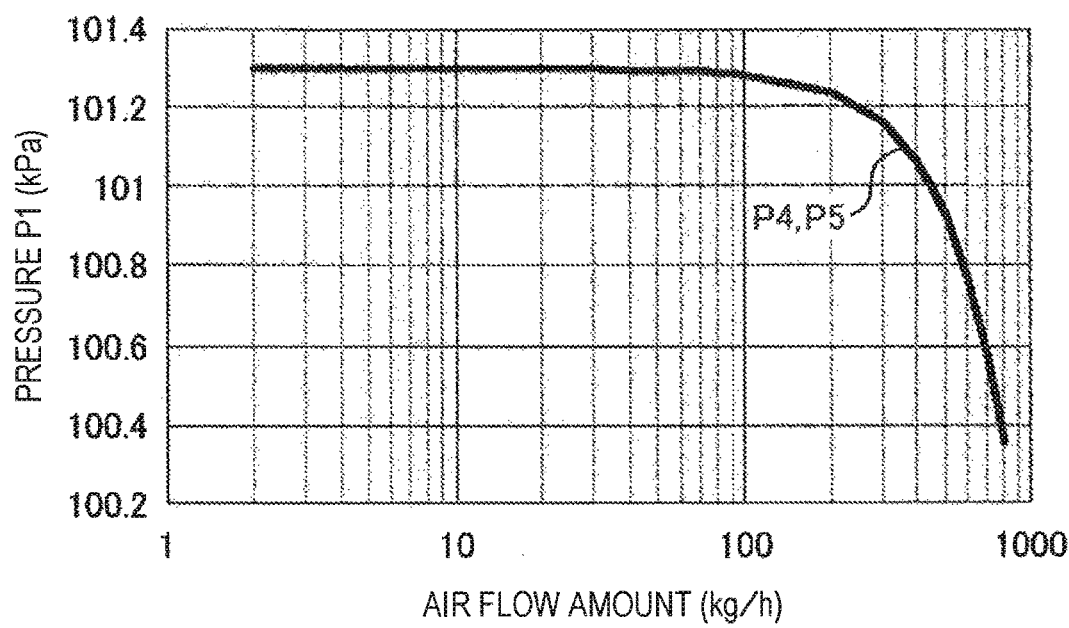
FIG. 7B is a graph indicating the pressure at the position of the humidity sensor element and at the position of the pressure sensor element, in the system illustrated in FIG. 6B.

Next, the systems of FIG. 6A and FIG. 6B will be described below in terms of the calculation results indicating the comparison between the pressure received by the humidity sensor element 4 and the pressure received by the pressure sensor element 5. FIG. 7A illustrates the pressures according to the system of FIG. 6A, while FIG. 7B illustrates the pressures according to the system in which the present invention is applied.

FIG. 7A indicates that the positions L5, L4 in the gas intake passage 2 provide the different pressures P4, P5, particularly in the large flow amount zone of 100 kg/h or higher. When the system of FIG. 6A is applied to correct the pressure dependency of the humidity sensor element 4 by using the detected pressure P5 of the pressure sensor element 5, the relation between the two pressures P5, P4 caused by the positional difference between the sensors 4, 5 have to be considered for a required correction calculation. In addition, it is necessary to set a fixed number of a correction calculation for each type of internal combustion engines, since each type has a gas intake passage of own shape, length and diameter. Furthermore, FIG. 7A indicates the calculation result of the intake gas pressure in a steady state with a constant flowing amount. The air in a gas intake passage of an internal combustion engine in actual use involves a pressure variation caused by a gas intake valve that opens and closes, and further involves a generation of pulsation in association with a backflow. Determination of the relation between the pressure P4 and the pressure P5 in response to the operation condition of an internal combustion engine to carry out a calculation correction requires an excessive amount of fixed numbers for corrections as well as an excessive amount of calculations. Moreover, continuous monitoring of the operation condition of an internal combustion engine (the rotation number, the condition of a throttle valve, the conditions of an intake and exhaust valves, and the like) is required for a selection of a fixed number for each condition for calculation, which adversely leads to a complicated system.

Contrary to the system described above, the system involving the present invention and illustrated in FIG. 6B is such that the humidity sensor element 4 and the pressure sensor element 5 are disposed in the measuring chamber 7 in which the air is fed through the common communication path 8. Thus, the pressure P4 at the position where the humidity sensor element 4 is located and the pressure P5 at the position where the pressure sensor element 5 is located have the same pressure value of the position where the gas sensor device 1 is located with the distance L. This allows, as illustrated in FIG. 7B, the humidity sensor element 4 and the pressure sensor element 5 to be constantly retained under the same pressure condition. Accordingly, the pressure P4 is identical to the pressure P5 in various operation conditions of internal combustion engines, which favorably avoids a preliminary arrangement of the relation between the pressure P4 and the pressure P5. In addition, continuous monitoring of the operation condition of an internal combustion engine (the rotation number, the condition of a throttle valve, the conditions of an intake and exhaust valves, and the like) becomes unnecessary, which enables a highly accurate humidity measurement with a simple system.

A more desired correction method will be described below, in which the humidity sensor element 4 in the embodiment is composed of an electrostatic capacitance type humidity sensor element. This type is adapted to detect the variation of a dielectric constant based on the increase and decrease of moisture in a moisture sensitive film.

Figure 8:
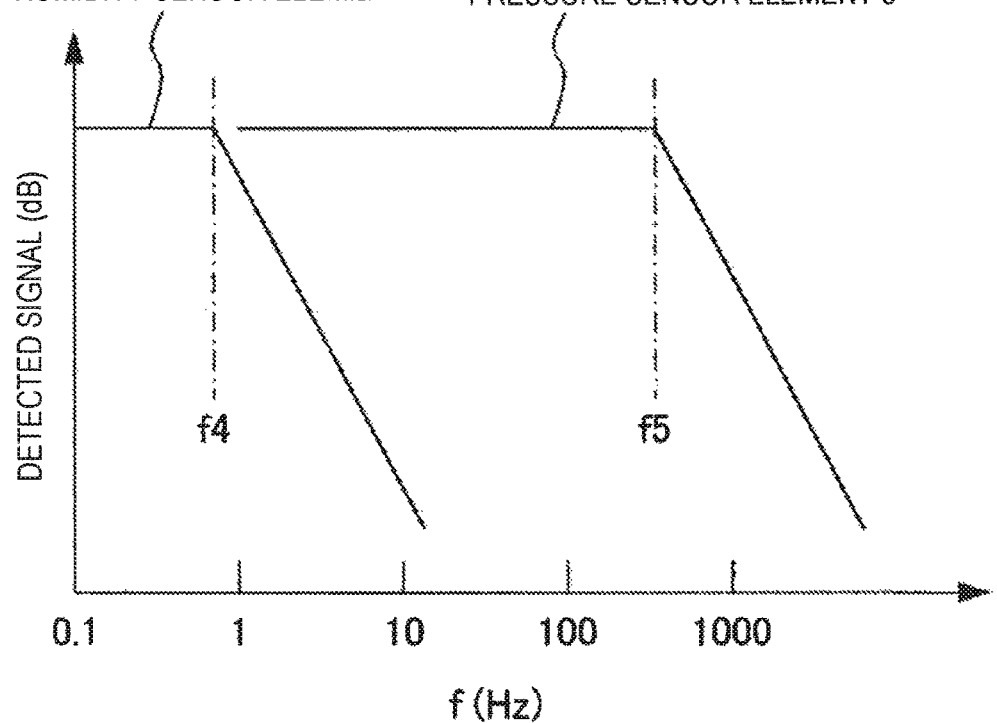
FIG. 8 is a graph indicating the responsiveness of the humidity sensor of an electrostatic capacitance type and the pressure sensor.

FIG. 8 illustrates a graph of a comparison between the responsiveness of an electrostatic capacitance type humidity sensor and the responsiveness of a general pressure sensor. The electrostatic capacitor type has a response speed of several seconds (1 Hz order), while the pressure sensor has a response speed of several milliseconds (1 kHz order). High speed rotation operation of an internal combustion engine generates an intake gas pulsation of about 100 Hz. The electrostatic capacitance type humidity sensor has a slow response speed and thus cannot follow the pressure variation caused by the intake gas pulsation of 100 Hz. Unlike the electrostatic capacitance type humidity sensor, the pressure sensor sufficiently follows such pressure variation. Carrying out a correction of the humidity sensor in an intake gas pulsation period by using the pressure sensor having a high response speed adversely carry out an unnecessary correction, whereby the corrected humidity signal can be deteriorated in its accuracy. That is, the correction undesirably overlaps a high frequency signal on the signal of the humidity sensor.

To overcome the problem mentioned above, an effective method is to process a detected signal of the pressure sensor element 5 illustrated in FIG. 5 by the signal processing unit FLT2. The signal processing unit FLT2 preferably functions to remove or attenuate a high frequency component of a pressure signal exceeding the response speed of the humidity sensor 4 illustrated in FIG. 8. For the method to remove or attenuate a high frequency component, a low pass filter having a time constant corresponding to the response speed of the humidity sensor 4 may be used. Additionally, another method may be an averaging processing in which time is averaged in response to the response speed of the humidity sensor element 4. Those methods can reduce unnecessary correction during a high frequency pulsation, thereby providing a highly accurate humidity signal (output).

More specifically, this embodiment includes a response speed adjusting means (response speed adjusting unit) that adjusts the difference in the response speeds between a detected signal of the humidity sensor element 4 and a detected signal of the pressure sensor element 5. The response speed adjusting means is configured by the signal processing unit FLT2. The response speed adjusting means functions to bring the response speed of a detected signal (pressure signal) of the pressure sensor close to the response speed of a detected signal (concentration signal) of the concentration sensor. A low pass filter, when used as the response speed adjusting means, is arranged such that the cutoff frequency thereof is set between the frequency f4 corresponding to the response speed of the humidity sensor element 4 and the frequency f5 corresponding to the response speed of the pressure sensor element 5 (which is equal to or higher than f4 and is smaller than f5, and is preferably higher than f4 and lower than f5). In this arrangement, the cutoff frequency is preferably closer to the side of f4 than to the side of f5. In the case of the averaging processing, a fluctuation portion present between the frequency f4 and the frequency f5 is removed or attenuated by the processing. In the above description, the break points shown up in the response characteristic of FIG. 8 are designated as the frequency f4 and the frequency f5, respectively. However, such break points do not appear in reality, and thus the frequencies attenuated 3 dB from the maximum value are designated as the frequency f4 and the frequency f5, respectively.

Second Embodiment

Figure 9:
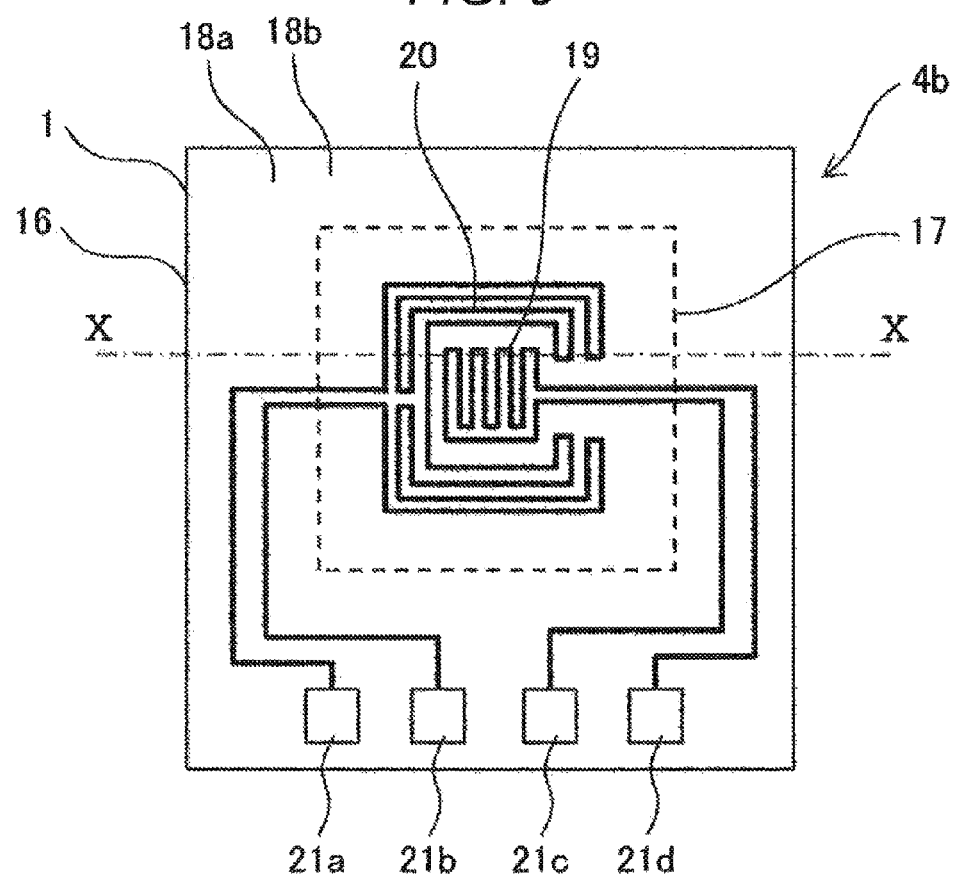
FIG. 9 is a plan view illustrating a thermal humidity sensor according to a second embodiment of the present invention.
Figure 10:
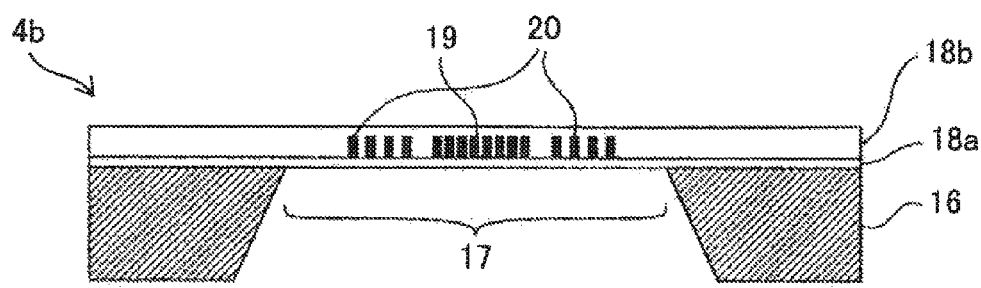
FIG. 10 is a cross sectional view along the line X-X in FIG. 9.
Figure 11:
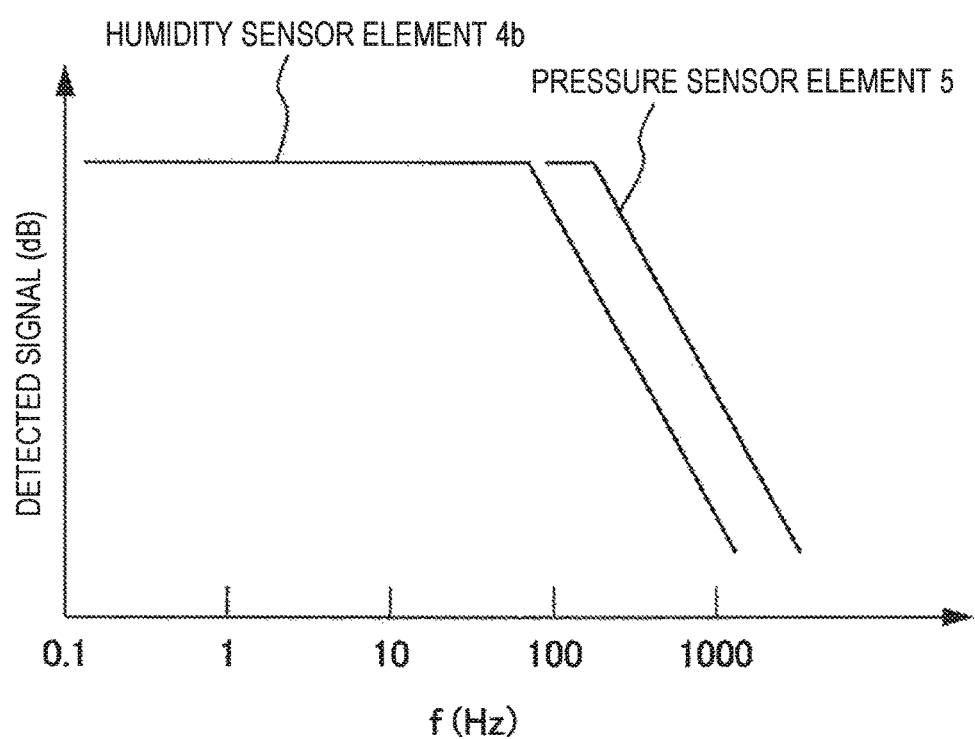
FIG. 11 is a graph indicating a comparison of the responsiveness between the thermal humidity sensor and the pressure sensor.

With reference to FIGS. 9 to 11, a further preferable gas sensor device according to a second embodiment applied with the present invention will be described.

The second embodiment has such a characteristic that a thermal humidity sensor element capable of measuring the absolute humidity is applied as the humidity sensor element.

FIG. 9 illustrates a plan view of a thermal humidity sensor that is suitable to obtain the effects of the present invention. FIG. 10 illustrates a cross sectional view along the line X-X in the sensor element 4b of FIG. 9.

The thermal humidity sensor in the embodiment includes a humidity sensor element 4b provided with a substrate 16 made of single crystal silicon. The substrate 16 includes a concave portion 17 covered with an insulation film 18a. The insulation film 18a is provided thereon with heat generating bodies (heat resisting bodies) 19, 20. The heat generating bodies 19, 20 are placed on the insulation film 18a in the concave portion 17. The heat generating bodies 19, 20 each have a surface that is covered with an insulation film 18b for protection. The heat generating bodies 19, 20 are provided with electrodes 21a-21d for a supply and a takeout of voltages and currents. The electrodes 21a-21d are electrically connected to a heat control device (not illustrated) through gold wire bonding wires or lead frames.

Selected materials having a high temperature coefficient resistance for the heat generating bodies 19, 20 include, for example, platinum (Pt), tantalum (Ta), molybdenum (Mo) and silicon (Si). Materials to be selected for the insulation layers 18a, 18b include silicon oxide (SiO2) and silicon nitride (Si3N4), which are used individually or in combination in a layered structure. In addition, selected materials for the insulation layers 18a, 18b may be resin materials such as polyimide, ceramic and glass, which can be of any combination. Furthermore, materials to be selected for the electrodes 21a-21d include aluminum (Al), aurum (Au) and the like.

The heat generating bodies 19, 20, the concave portion 4, the insulation films 18a, 18b and the electrodes 10a-10f are formed by means of a semiconductor fine processing technique, in which a photolithography is used, or an anisotropic etching technique.

The measurement principle of the thermal humidity sensor in the embodiment will be described below.

The heat resisting body 19 is heated to and controlled at about 400° C. to 500° C., while the heat resisting body 20 is heated to and controlled at 200° C. to 300° C. Variation of the humidity of the air changes the thermal conductivity of the air, thereby changing the amount of heat released from the heat resisting body 19 into the air. Detection of the variation of the amount of heat released allows the measurement of the absolute humidity. The heat resisting body 20 functions as a heat generating body that helps the temperature around the heat resisting body 19 retained constant. Thanks to the heat resisting body 20, the temperature around the heat generating body 19 can be retained constant even if the temperature of the air surrounding the sensor element 4b changes, thereby providing an improved temperature characteristic in the humidity measurement. This embodiment includes the heat resisting body 20; however, the heat resisting body 19 alone can carry out the humidity measurement. In case a single number of heat resisting body is used, a temperature sensor to be required can be used to additionally compensate a measurement error due to temperature variation, whereby the compensation of the temperature characteristic can be enabled.

The thermal humidity sensor according to this embodiment is characterized to have a small thermal capacitance by configuring the concave portion 17 to provide a thin film portion on which the heat resisting body 19 is placed. This configuration allows the sensor to have a high speed response with respect to the variation of the thermal conductivity of the air. Other humidity sensor elements besides the thermal humidity sensor element include the aforementioned electrostatic capacitance type element. The electrostatic capacitance type element, however, has a slow response because of its detection principle such that the variation of the dielectric constant is detected on the basis of the increase and decrease of the moisture in a moisture sensitive film formed on a substrate. With respect to the humidity variation, the electrostatic capacitance type has a response speed of about 5 to 10 seconds, while the thermal humidity sensor has a response speed of less than several tens of milliseconds.

The gas sensor device provided with the thermal humidity sensor of the embodiment has the following operations and effects, which will be described below. As described above, the thermal humidity sensor has a high speed response characteristic, and in addition to that, the sensor also has a high speed response with respect to the pressure variation. The responsiveness of the humidity sensor element has importance in a pressure correction in which a pressure sensor is used.

FIG. 11i illustrates a graph in which the responsiveness of a thermal humidity sensor is compared with the responsiveness of a general pressure sensor. The thermal humidity sensor element 4b and the pressure sensor have a response speed of several milliseconds to several tens of milliseconds (100 Hz to 1 kHz). Specifically, the thermal humidity sensor and the pressure sensor have substantially the similar responsiveness. High speed operation of an internal combustion engine generates an intake gas pulsation of about 100 Hz that can be easily followed by the thermal humidity sensor 4b and the pressure sensor. Thus, in use of the thermal humidity sensor element 4b, a detected value of the thermal humidity sensor element 4b can be corrected by using a detected value of the pressure sensor element 5, even in an intake gas pulsation period of a high frequency. This allows a highly accurate measurement of an instantaneous value of the absolute humidity, even in an intake gas pulsation period of a high frequency.

Additional application of the signal processing unit FLT1 for a detected signal of the humidity sensor element 4 and the signal processing unit FLT2 for a detected signal of the pressure sensor element 5, which are illustrated in FIG. 5, provides further improved accuracy. The thermal humidity sensor 4b has an element of high speed; however, the response speed thereof is slightly different from that of the pressure sensor element 5. Therefore, the signal processing units FLT1, FLT2 are used to bring the response speed of the pressure sensor element 5 close to the response speed of the humidity sensor element 4b, or bring the response speed of the humidity sensor element 4b close to the response speed of the pressure sensor element 5. With such a processing, the pressure sensor element 5 and the thermal humidity sensor element 4b come to the same characteristic, thereby providing easier correction and improved accuracy. In some cases, the thermal humidity sensor element 4b is controlled so as to have a slower response speed by changing a control characteristic of the heat resisting body 19, particularly in an internal combustion engine of automobiles and in response to the operation condition of the engine. Such a case can lead to an increased variation between the response speed of the thermal humidity sensor element 4b and the response speed of the pressure sensor element 5. The signal processing unit FLT2 is effective as a response speed adjusting means (response speed adjusting unit) that brings the response speed of the pressure sensor element 5 close to the response speed of the humidity sensor element 4b.

In this embodiment, the thermal humidity sensor element 4b is used as a humidity sensor 4, while the remaining components are composed of the same members as the first embodiment. It should be noted that the condition of each component of the processing circuit 14 is adjusted with consideration of the response speed of the thermal humidity sensor element 4b.

Third Embodiment

An embodiment in which the present invention is applied to a composite sensor device will be described, the composite sensor integrally including an air flow meter disposed in a gas intake passage of an internal combustion engine and an environmental sensor used for the temperature and the humidity. The composite sensor device of the embodiment to be described below integrally includes, as one example, an intake gas flow sensor, an intake gas temperature sensor, a humidity sensor and a pressure sensor.

Figure 12:
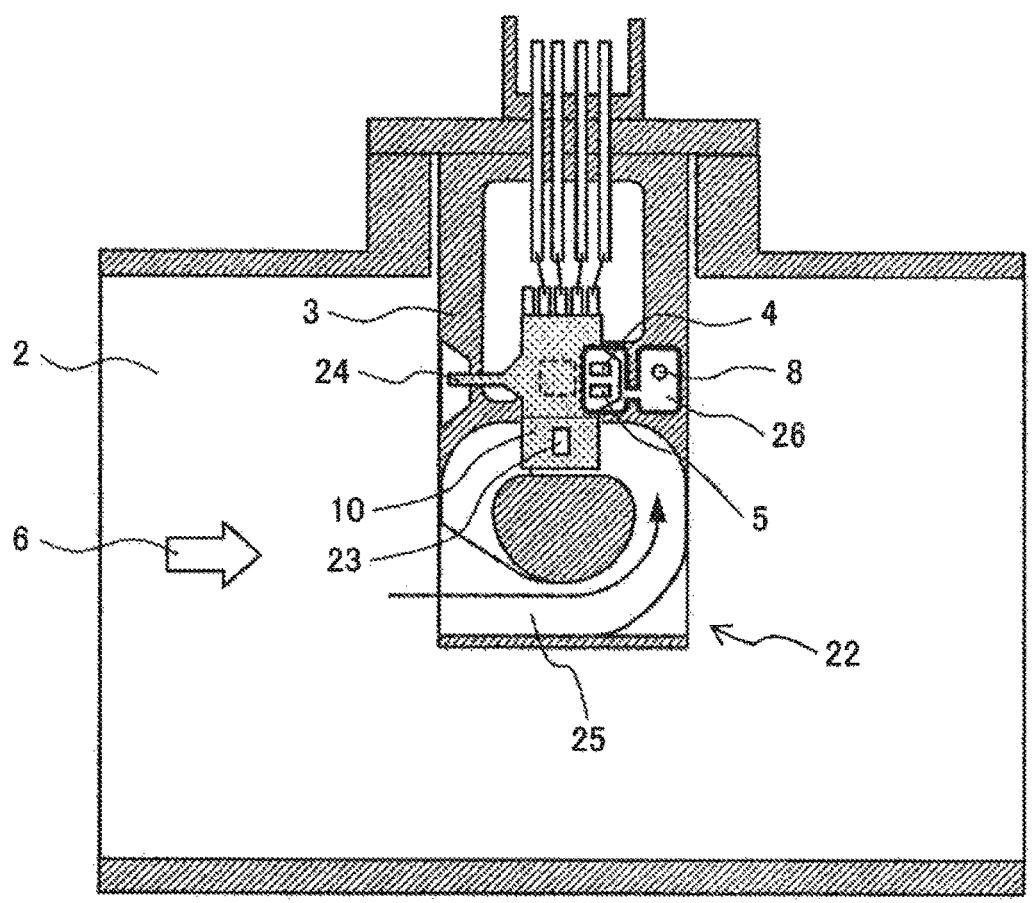
FIG. 12 is a cross sectional view of a gas sensor device according to a third embodiment of the present invention and a structure in which the gas sensor device is installed.

FIG. 12 illustrates a cross sectional view of a composite sensor device 22 of the embodiment and a structure in which the device is installed. The composite sensor device 22 in FIG. 12 is installed in a gas intake passage 2 of an internal combustion engine so as to protrude inside the passage 2. The composite sensor device 22 includes a housing 3 that incorporates a humidity sensor element 4, a pressure sensor element 5, a flow amount sensor element 23 and an intake gas temperature sensor element 24. The flow amount sensor element 23 is composed of a thermal type element including a semiconductor substrate, a thin film portion formed on the substrate and a heat generating body (heat resisting body) provided to the thin film portion, wherein the flow amount is measured by the variation of the amount of heat released from the heat generating body or the variation of the temperature distribution around the heat generating body. The gas intake temperature sensor element 24 may be composed of a thermistor or a temperature measuring resistor. The humidity sensor element 4, the pressure sensor element 5, the flow amount sensor element 23 and the intake gas temperature sensor element 24 are integrated into a same sensor package 10.

The housing 3 includes a sub-passage 25 that is arranged to separate the air flow inside the gas intake passage 2 and includes the flow amount sensor element 23 disposed in a protruding manner. The sensor package 10 partially has a beam shape extending outwardly of the housing 3, and the beam shape is provided at a distal end thereof with the gas intake temperature sensor element 24.

Figure 13:
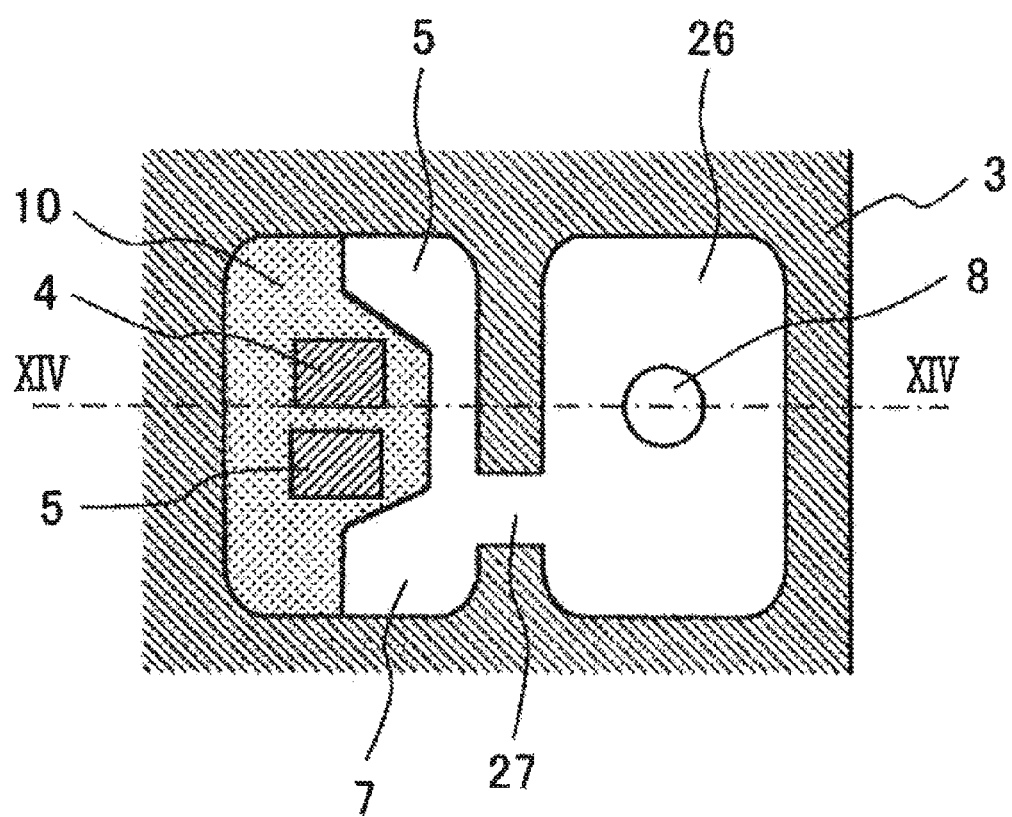
FIG. 13 is an enlarged view of the humidity sensor element and a surrounding thereof illustrated in FIG. 12.

FIG. 13 illustrates an enlarged view of an area of FIG. 12, where the humidity sensor element 4 and the pressure sensor element 5 are located. The humidity sensor element 4 and the pressure sensor element 5 are disposed in a measuring chamber 7 (first concave portion) provided inside the housing 3. The measuring chamber 7 communicates, via a communication portion 27, with an expansion chamber 26 (second concave portion) provided inside the housing. The expansion chamber 26 includes a communication path 8 opening to the gas intake passage 2. The communication path 8 is provided to the housing 3 at a surface (side surface) thereof, the surface extending along the flow of the gas intake passage 2. The volume changes from the communication path 8 to the humidity sensor element 4 in such a manner, similar to the first embodiment, that the volume is contracted by the communication path 8 at the opening portion communicating to the gas intake passage 2, expanded in the expansion chamber 6, contracted at the communication portion 7, and expanded in the measuring chamber 5.

Figure 14:
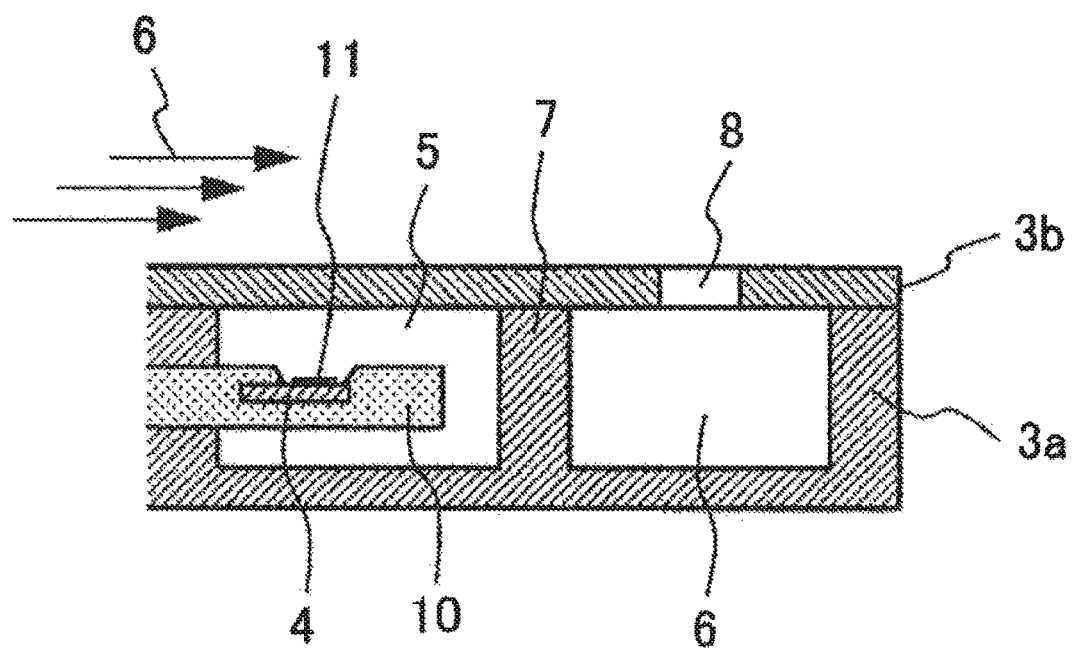
FIG. 14 is a cross sectional view along the line XIV-XIV in FIG. 13.

FIG. 14 illustrates a cross sectional view along the line XIV-XIV in FIG. 13. The humidity sensor element 4 and the pressure sensor element 5 in FIG. 14 are secured by the sensor package 10 that serves as a supporting member. The supporting member 10 is composed of a mold package manufactured by an injection molding technique. The humidity sensor element 4 includes a detecting unit 11 that is configured so as to be exposed from the package. The supporting member 10 is covered with a base 3a and a cover 3b. The base 3a and the cover 3b together configure the housing 3. The base 3a and the cover 3b are molded, adhered or joined with each other so as to configure the measuring chamber 7, the expansion chamber 26, the communication portion 27 and the communication path 8.

Next, the structure of the sensor package 10, which is mold packaged, will be described.

Figure 15A:
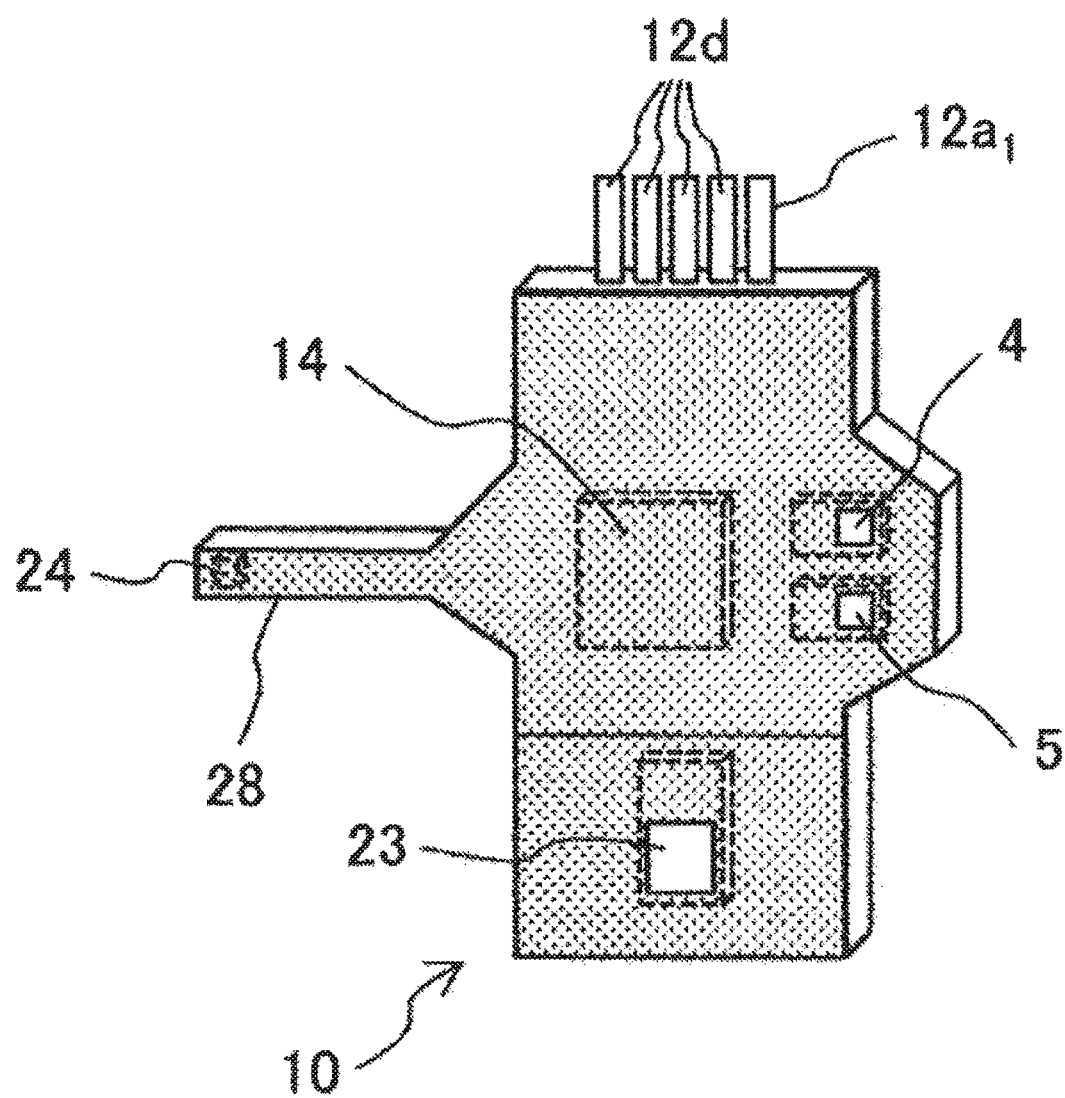
FIG. 15A illustrates an outlook appearance of a sensor package in a mold packaged form.

FIG. 15A illustrates an outlook appearance of the sensor package 10. The humidity sensor element 4, the pressure sensor element 5 and the flow amount sensor element 21 are packaged with molding resin so that the detecting units thereof are exposed. The gas intake temperature sensor element 24 is embedded in a distal end of a beam 28 configured by a portion of the package, the portion being protruded. The package mounts inside thereof a semiconductor chip (processing circuit unit) 14 that carries out operations, detections and corrections of the humidity sensor element 4, the pressure sensor element 5, the flow amount sensor element 23 and the gas intake temperature sensor element 22. Lead frames $12d$, $12a_1$ have portions exposed from the package 10 and configuring terminals that are used to supply power to those elements and to output signals detected by the semiconductor chip 14.

Figure 15B:
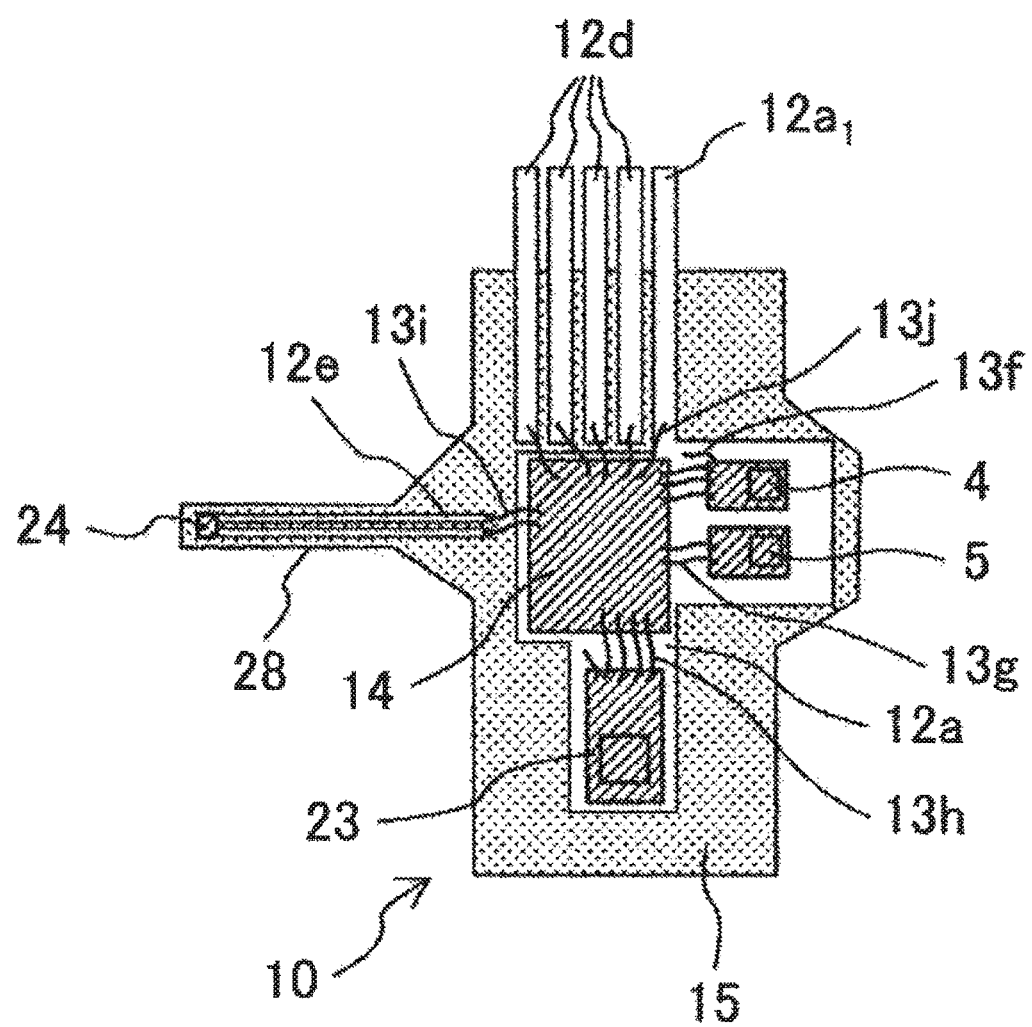
FIG. 15B illustrates a structure of the sensor package in a mold packaged form.

FIG. 15B illustrates an internal structure of the sensor package 10. The humidity sensor element 4, the pressure sensor element 5, the flow amount sensor element 21 and the semiconductor chip 14 are adhered and secured on the lead frame 12a. The gas intake temperature sensor element 24 is disposed at a distal end of a lead frame 12e extending with the beam 28. The humidity sensor element 4 has an electrode that is electrically connected to the semiconductor chip 14 through bonding wires 13f. The pressure sensor element 5 has an electrode that is electrically connected to the semiconductor chip 14 through bonding wires 13g. Similarly, the flow amount sensor element 23 is connected to the semiconductor chip 14 through bonding wires 13h. The gas intake temperature sensor element 24 is electrically connected to the semiconductor chip 14 by connecting the lead frame 12e to the semiconductor chip 14 via bonding wires 13i.

The power source of the semiconductor chip 14 and the detected signals are connected to the lead frames 12d, $12a_1$ via bonding wires 13j, and the electrodes thereof are pulled outside the package 10. In this embodiment, the lead frame $12a_1$ is designated as a common grounding terminal and is used as a member for mounting thereon the humidity sensor element 4, the pressure sensor element 5, the flow amount sensor element 21 and the semiconductor chip 14.

Figure 16:
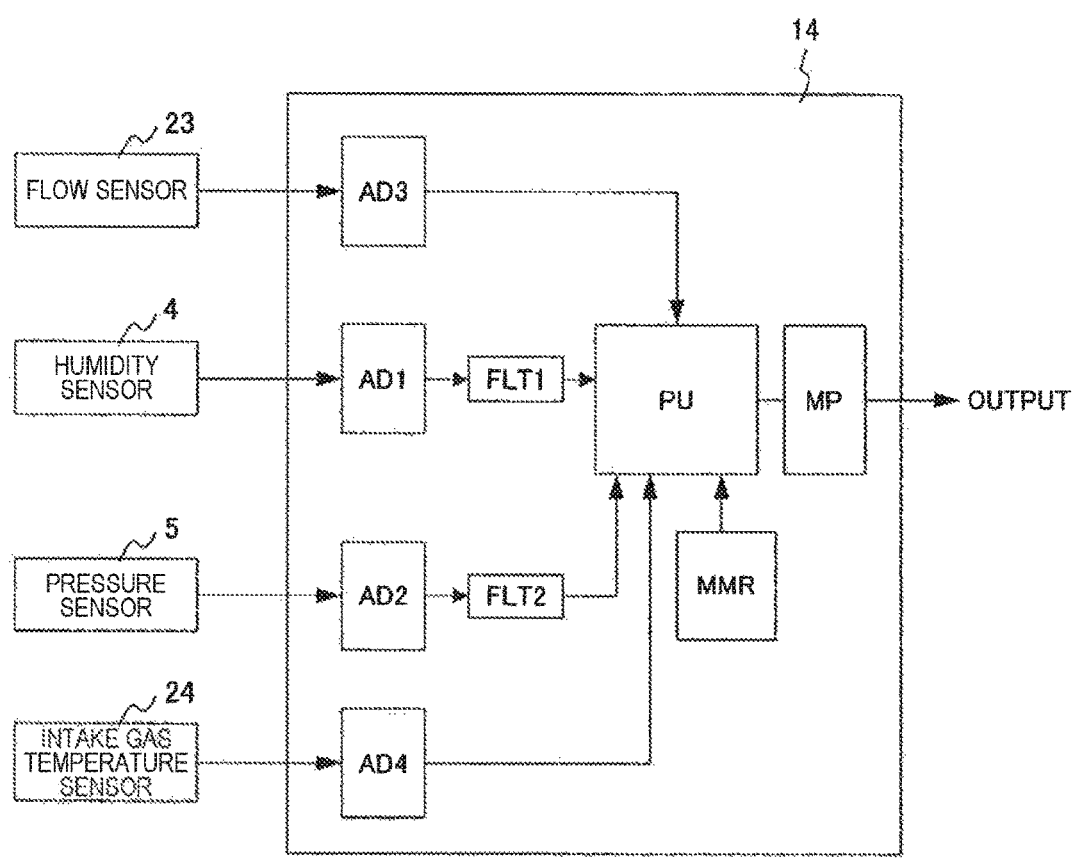
FIG. 16 is a block diagram illustrating a processing mode of a sensor signal in the third embodiment of the present invention.

FIG. 16 illustrates a processing mode of sensor signals of the semiconductor chip 14 according to the embodiment. The semiconductor chip 14 includes an A/D converter AD1 which inputs an analog signal sent from the humidity sensor 4 and converts the input signal into a digital value and an A/D converter AD2 which inputs an analog signal sent from the pressure sensor element 5 and converts the input signal into a digital value. The humidity signal converted into the digital value in the A/D converter AD1 is subjected to the removal of a signal noise in a signal processing unit FLT1 and is then input in a calculation unit PU. The pressure signal converted into the digital value in the A/D converter AD2 is subjected to the removal of a signal noise in the signal processing unit FLT2 and the abovementioned response speed adjustment, and is then input in the calculation unit PU. The processing mode further includes an A/D converter AD3 which inputs an analog signal sent from the flow amount sensor element 21 and converts the input signal into a digital value and an A/D converter AD4 which inputs an analog signal sent from the intake gas temperature sensor element 24 and converts the input signal into a digital value. The calculation unit PU carries out a correction calculation of the humidity signal. The correction calculation determines the amount of correction on the basis of the pressure signal value and a fixed number stored in advance in a memory unit MMR, and the determined correction amount is added to the humidity signal. Then, the humidity signal corrected in the calculation unit PU is output as OUTPUT. In this embodiment, a variety of information can be measured by the sensors, and thus the embodiment is provided with an output circuit MP for outputting the measured sensor signals. The output circuit MP is provided with a multiplexer function that selects any sensor signal and outputs the selected signal, or a function that superimposes a plurality of sensor signals or power voltage on a single output signal line.

The processing circuit 14 in this embodiment carries out an adjustment-processing of the response speed variation between the detected signal of the humidity sensor element 4 and the detected signal of the pressure sensor element 5, which processing is described in the first and second embodiments.

The configuration in this embodiment has a composite structure consisting of the flow amount sensor element 21, the gas intake temperature sensor 24, the humidity sensor element 4 (4b) and the pressure sensor element 5, and the semiconductor chip 14 provided with a digital correction function is able to mutually correct the signal of each element to thereby provide highly improved accuracy. For example, the signal of the flow amount sensor element 21 can be additionally given the corrections for humidity dependency and pressure dependency.

In addition, the humidity sensor element 4 and the flow amount sensor element 21 are combined together, and thus the composition thereof can measure the flow-in amount of moisture contained in the air, in addition to the air flow amount. The thermal humidity sensor element 4b used as a humidity sensor element 4 allows an easy measurement of the absolute humidity, a further highly accurate measurement of the flow-in amount of moisture contained in the air, and an optimal control of the combustion of an internal combustion engine.

Moreover, the thermal humidity sensor element 4b has an excellent characteristic in use in a high temperature environment and a high humidity environment, and thus it can provide a gas sensor device with highly improved accuracy and reliability in a severe environmental use. Such a gas sensor device can be mounted inside a gas intake passage 2 that includes a supercharger at a downstream side of the passage in an internal combustion engine, and that is involved in the increased and reduced pressures being repeated and stain substances such as oil flowing in the passage.

Each of the embodiments described above is arranged such that the concentration sensor (including the humidity sensor) and the pressure sensor are disposed in the same space having the same pressure, which arrangement allows an accurate correction in which an accurate pressure value is used. This, therefore, can achieve appropriate correction results under a variety of operation conditions of an internal combustion engine. In addition, the gas sensor device alone can correct the pressure, which can reduce the number of man-hours for adjusting the gas sensor device for an internal combustion engine. Furthermore, the gas sensor device allows a reduced number of man-hours for adjusting the gas sensor device to different types of vehicles having respective different sensor positions and gas intake shapes.

It should be noted that the present invention is not limited to the embodiments described above and can include various modifications thereof. For example, the abovementioned embodiments are described in detail for easy understanding of the present invention, and the present invention should not be limited to a configuration in which all of the components or members described above are included. In addition, one of the embodiments can be partially replaced by a configuration of another embodiment, and can be additionally provided with a configuration of another embodiment.

Furthermore, each of the embodiments can have a configuration part of which is additionally provided with, removed or replaced with a configuration of another style.

Moreover, the abovementioned configurations, functions, processing units and processing means may be achieved entirely or partially by hardware such as a so designed integrated circuit, for example. Instead, the abovementioned configurations, functions, processing units and processing means may be achieved by software where processors read and carry out respective programs designed to realize respective functions.

The controlling lines and the information lines introduced are those considered to be necessary in the descriptions, and not all the controlling lines and the information lines are essentially necessary in products. In actual use, almost all of the components are considered to be connected with one another.

REFERENCE SIGNS LIST 1 sensor device
2 gas intake passage
3 housing
3a base
3b cover
4, 4b humidity sensor element
5 pressure sensor element
6 intake gas
7 communication path
8 gas intake opening
10 sensor package
11 detecting unit
12 lead frame
13 wire
14 semiconductor chip
15 sealing resin
16 substrate
17 concave portion
18 insulation film
19, 20 heat generating body
21 electrode
22 composite sensor device
23 flow amount sensor element
24 intake gas temperature sensor element
25 sub-passage
26 expansion chamber
27 communication portion
28 beam

The invention claimed is:

1. A gas sensor device including a concentration sensor for measuring concentration of gas and a pressure sensor for measuring a pressure of the gas, the device comprising:
 a housing;
 a measuring chamber provided inside the housing, the measuring chamber being isolated from an air flow; and
 a processing circuit unit that adjusts a signal of the concentration sensor using a signal of the pressure sensor, wherein
  the concentration sensor and the pressure sensor are disposed in the measuring chamber,
  the processing circuit unit includes a response speed adjusting unit arranged to bring a response speed of a pressure signal of the pressure sensor close to a response speed of a concentration signal of the concentration sensor,
  the response speed adjusting unit has a function to remove or attenuate a high frequency signal component from a pressure signal sent from the pressure sensor, the high frequency signal component being higher than a frequency corresponding to the response speed of a concentration signal of the concentration sensor, and
  the concentration signal is corrected by a pressure signal adjusted by the response speed adjusting unit.

2. The gas sensor device according to claim 1,
 wherein the processing circuit unit includes a first A/D converter and a second A/D converter, the first A/D converter inputting a concentration signal sent from the concentration sensor and converting the input concentration signal into a first digital value, the second A/D converter inputting a pressure signal sent from the pressure sensor and converting the input pressure signal into a second digital value,
 the response speed adjusting unit has a function to remove or attenuate the high frequency signal component from the pressure signal converted into the second digital value, and
 the gas sensor device further comprises a calculation unit, the calculation unit performing a correction calculation of the concentration signal converted into the first digital value by the first A/D converter, the correction calculation being performed based on the pressure signal from which the high frequency signal has been removed or attenuated by the response speed adjusting unit.

3. The gas sensor device according to claim 2, wherein the measuring chamber includes a communication path communicating the measuring chamber with an external space in which gas to be measured flows, the communication path being provided to a surface of the housing, the surface extending along the flow of the gas.

4. The gas sensor device according to claim 3, wherein the concentration sensor measures the concentration of gas by utilizing an event that an amount of heat released from a heat resisting body varies depending on the concentration of the gas.

5. The gas sensor device according to claim 4, wherein the heat resisting body of the concentration sensor is provided on a thin part formed in a semiconductor substrate.

6. The gas sensor device according to claim 1,
 wherein the concentration sensor is configured to measure a humidity of the gas and output a humidity signal, and
 the housing integrally includes a flow amount sensor element and a gas intake temperature sensor element, and the humidity signal or the pressure signal is used to correct a flow amount signal of the flow amount sensor element.

* * * * *